United States Patent [19]

Taylor et al.

[11] Patent Number: 4,684,653

[45] Date of Patent: Aug. 4, 1987

[54] PYRIDO(2,3-D)PYRIMIDINE DERIVATIVES

[75] Inventors: Edward C. Taylor, Princeton, N.J.; George P. Beardsley, Essex, Conn.; Peter J. Harrington, Endicott, N.Y.; Stephen R. fletcher, Buckinghamshire, England

[73] Assignee: The Trustees of Princeton University, Princeton, N.J.

[21] Appl. No.: 835,457

[22] Filed: Mar. 3, 1986

Related U.S. Application Data

[63] Continuation-in-part of Ser. No. 709,622, Mar. 8, 1985, abandoned.

[51] Int. Cl.$^4$ .................. A61K 31/505; C07D 471/04; C07D 475/04; C07D 475/08
[52] U.S. Cl. .................................... 514/258; 544/279; 544/260
[58] Field of Search ......................... 544/279; 514/258

[56] References Cited

U.S. PATENT DOCUMENTS

| | | | |
|---|---|---|---|
| 3,856,959 | 12/1974 | Mead | 424/251 |
| 4,172,200 | 10/1979 | Piper et al. | 544/260 |
| 4,369,319 | 1/1983 | DeGraw et al. | 544/260 |
| 4,431,805 | 2/1985 | Temple et al. | 544/279 |
| 4,432,981 | 2/1984 | Lesher et al. | 424/251 |
| 4,460,591 | 7/1984 | DeGraw et al. | 424/251 |
| 4,512,992 | 4/1985 | Duch et al. | 514/258 |
| 4,526,964 | 7/1985 | Temple et al. | 544/279 |
| 4,532,241 | 7/1985 | DeGraw et al. | 514/258 |
| 4,536,575 | 8/1985 | Temple et al. | 544/279 |
| 4,564,616 | 1/1986 | Jones et al. | 514/260 |

FOREIGN PATENT DOCUMENTS 1534238 11/1978 United Kingdom .

OTHER PUBLICATIONS

Moad et al., JACS 101:20, 6068–6076, (9/27/76).
Jahine et al., Ind. J. Chem., 16B, 889–891, (10/78).
Sirotnak et al., Cancer Treat. Rep., 66:2, (2/82).
Troschütz et al., Arch. Pharm. 331, 406–414, (1978).
Temple et al., J. Org. Chem 47, 761–764.
Taylor et al., J. Org. Chem. 50, 1010–1014, (1985).
Taylor et al., Chem. & Biology of Pteridines (Ed. J. A. Blair) 1983 Walter de Gruyter & Co., N.Y., 115–119.
Taylor et al., J. Org. Chem. 48, 4852–4860, (1983).
Taylor et al., J. Org. Chem. 50, 1005–1010, (1985).
DeGraw et al., J. Heterocycl. Chem. 19, 1461–1463, (1982).
Grivsky et al., J. Med. Chem. 23:3, 327–329, (1980).
Piper et al., J. Med. Chem. 23, 320–321, (1980).
DeGraw et al., J. Med. Chem. 17:5, 552–553, (1974).
Elliott et al., J. Med. Chem. 17:5, 553–555, (1974).
Nair, J. Org. Chem. 50, 1879–1884, (1985).
Drugs of the Future, IV, No. 9, 641–644, (1979).
Sirotnak et al., Cancer Treat. Rep. 62:7, 1047–1052, (1978).
Stone et al., Biochem. Pharmac. 33:2, 175–179, (1984).
Srinivasan et al., J. Org. Chem., 45, 3746–3748, (1980).
Hurlbert et al., J. Med. Chem., 11, 703–707, (1968).
Hurlbert et al., J. Med. Chem., 11, 708–710, (1968).
Hurlbert et al., J. Med. Chem., 11, 711–717, (1968).
Rosowsky et al., J. Med. Chem. 17:12, 1272–1276, (1974).
Struck et al., J. Med. Chem., 14:8, 693–695, (1971).
CA 96:104757a, (1982) Sirotnak et al.
Taylor et al., J. Med. Chem. 28:7, 914–921, (1985).
DeGraw et al., J. Heterocycl. Chem. 8, 105–110, (1971).
Oakes et al., J. Chem. Soc. (London) 4433, (1956).
Elsiager et al., Lectures in Heterocyclic Chemistry, vol. 2, S–97; Supplement to J. Heterocyclic Chem., 11, (1974).
Harrington, Synthetic Approaches to 5–Deaza and 5,10–Dideazafolic Acid Analogs, Ph.D. Dissertation, Princeton U., 1982.
De Graw et al., (VII), J. Med. Chem., 17:470, (1974).
DeGraw et al., (VIII), J. Heterocyclic Chem., 13:439, (1976).
Smith et al., Biochem. 20: 1241, (1981).
Temple et al. (V), J. Med. Chem. 24: 1254, (1981).
DeGraw et al.(IX), Chem. & Biolog. of Pteridines (Ed. Kisliuk/Brown) 1979 Elsevier, North Holland, (229–234).
Srinivasan et al. (II), J. Oreg. Chem. 46: 1777, (1981).
Srinivasan et al. (III), Tetrahedron Lett. 23:1431, (1982).
DeGraw et al. (X), PCT Application WO85/02844 (Published July 4, 1985).
Wheeler et al., J. Amer. Chem. Soc. 74:4725, (1952).
Kisliuk, R. L., Nature, 188:584, (1960).
Kisliuk et al. (II), J. Biol. Chem. 239: 1900, (1964).
Horwitz et al., J. Med. Chem. 11:907, (1968).
Chemical Abstracts, vol. 102 (1985): 125096S.

*Primary Examiner*—Donald G. Daus
*Assistant Examiner*—Barbara Cassatt
*Attorney, Agent, or Firm*—Bruce M. Collins

[57] ABSTRACT 2,4-Diamino- and 2-amino-4-hydroxy- derivatives of N-(4-[1-(pyrido[2,3-d]pyrimidin-6-yl)alk-2-yl]-benzoyl)-L-glutamic acids, and the corresponding 5,6,7,8-tetrahydro compounds are antineoplastic agents.

The compounds are prepared by hydrolytic or hydrogenolytic removal of carboxylic acid protecting groups from the correspondingly protected glutamic acid derivatives.

A typical embodiment is N-(4-[2-(2-amino-4-hydroxy-5,6,7,8-tetrahydropyrido[2,3-d]pyrimidin-6-yl)ethyl]-benzoyl)-L-glutamic acid.

16 Claims, No Drawings

PYRIDO(2,3-d)PYRIMIDINE DERIVATIVES

CROSS REFERENCE

This is a continuation-in-part of Ser. No. 709,622 filed Mar. 8, 1985, now abandoned.

TECHNICAL FIELD

The invention pertains to derivatives of N-(4-[2-(pyrido[2,3-d]pyrimidin-6-yl)alkyl]benzoyl)-L-glutamic acid, which derivatives are antineoplastic agents, and to their preparation and use.

BACKGROUND ART

The folic acid antimetabolites aminopterin and amethopterin (also known as 10-methylaminopterin or methotrexate) are antineoplastic agents. These compounds inhibit enzymatic conversions involving metabolic derivatives of folic acid. Amethopterin, for example, inhibits dihydrofolate reductase, an enzyme necessary for the regeneration of tetrahydrofolate from the dihydrofolate which is formed during the conversion of 2-deoxyuridylate to thymidylate by the enzyme thymidylate synthetase.

Other derivatives of folic acid and aminopterin have been synthesized and tested as antimetabolites. Among these are various "deaza" compounds in which a methylene or methylidene group occupies a position in the molecule normally occupied by an imino or nitrilo group, respectively. These derivatives have varying degrees of antimetabolic activity. 10-Deazaaminopterin is highly active (Sirotak et al., *Cancer Treat. Rep.*, 1978, 62, 1047) whereas 10-deazafolic acid shows no significant activity (Struck et al., *J. Med. Chem.*, 1971, 14, 693). 5-Deazafolic acid is only weakly cytotoxic whereas 5-deazaaminopterin has activity similar to that of amethopterin (Taylor et al., *J. Org. Chem.*, 1983, 48, 4852). 8,10-Dideazafolic acid is only marginally effective as a dihydrofolate reductase inhibitor (De Graw et al., "Chemistry and Biology of Pteridines", Elsevier, 1979, 229) while 5,8,10-trideazafolic acid also shows only marginal activity against mouse L1210 leukemia (Oatis et al., *J. Med. Chem.*, 1977, 20, 1393). 8,10-Dideazaaminopterin is reported to be active (U.S. Pat. No. 4,460,591) and 5,8,10-trideazaaminopterin exhibits activity against mouse L1210 leukemia (Yan et al., *J. Heterocycl. Chem.*, 1979, 16, 541).

DISCLOSURE OF INVENTION

The invention pertains to
(ia) pyrido[2,3-d]pyrimidines of the formula:

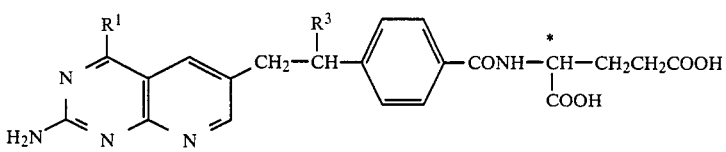

wherein
R¹ is amino or hydroxy; and
R³ is hydrogen, methyl, or ethyl; the configuration about the carbon atom designated * being L;
(ib) 5,6,7,8-tetrahydropyrido[2,3-d]-pyrimidines of the formula:

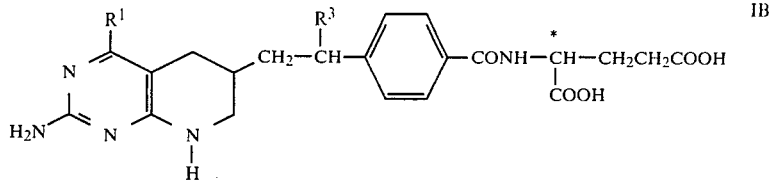

wherein
R¹ is amino or hydroxy; and
R³ is hydrogen, methyl, or ethyl; the configuration about the carbon atom designated * being L;
(ii) the tautomeric forms thereof; and
(iii) the pharmaceutically acceptable alkali metal, alkaline earth metal, non-toxic metal, ammonium, and substituted ammonium salts thereof.

The invention also pertains to methods for the preparation of such compounds, to intermediates useful in those preparations, and to methods and compositions for the use of such compounds in combatting neoplastic growth.

Modes For Carrying Out The Invention

The compounds of the invention are derivatives of the pyrido[2,3-d]pyrimidine heterocyclic ring which in numbered as follows:

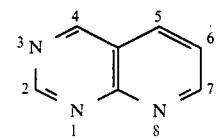

The compounds of Formulas IA and IB in which R¹ is hydroxy exist in tautomeric equilibrium with the corresponding 3,4-dihydro-4-oxo compounds.

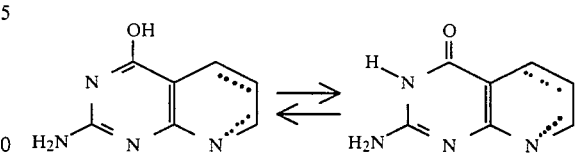

For convenience, the 4-hydroxy form is depicted and the corresponding nomenclature is used throughout this specification, it being understood that in each case such includes the tautomeric 3,4-dihydro-4-keto form.

The absolute configuration about the carbon atom designated * in the glutamic acid chain is L, being the same absolute configuration as that about the corresponding alpha carbon atom in alanine.

When $R^3$ is other than hydrogen, a second chiral center is present, thereby producing d,L- and 1,L-diastereoisomers. These can be separated mechanically, as by chromatography. In the case of the 5,6,7,8-tetrahydro compounds of Formula IB, the carbon atom in the 6-position of the pyrido[2,3-d]pyrimidine ring system also is a chiral center, leading to d,L- and 1,L-diastereoisomers if $R^3$ is hydrogen and to d,1,L-, d,d,L-, 1,1,L-, and 1,d,L-diastereoisomers if $R^3$ is other than hydrogen. All of the above forms, which can be separated as described above, are within the scope of the invention.

The invention includes the pharmaceutically acceptable alkali metal, alkaline earth metal, non-toxic metal, ammonium, and substituted ammonium salts, such as for example the sodium, potassium, lithium, calcium, magnesium, aluminum, zinc, ammonium, trimethylammonium, triethylammonium, triethanolammonium, pyridinium, substituted pyridinium, and the like.

The compounds of this invention have an effect on one or more enzymes which utilize folic acid, and in particular metabolic derivatives of folic acid, as a substrate. The following compounds are representative:

Compound No. 1. N-(4-[2-(2,4-diaminopyrido[2,3-d]pyrimidin-6-yl)ethyl]benzoyl)-L-glutamic acid.

Compound No. 2. N-(4-[2-(2-amino-4-hydroxypyrido[2,3-d]pyrimidin-6-yl)ethyl]benzoyl)-L-glutamic acid.

Compound No. 3. N-(4-[2-(2,4-diamino-5,6,7,8-tetrahydropyrido[2,3-d]pyrimidin-6-yl)ethyl]benzoyl)-L-glutamic acid.

Compound No. 4. N-(4-[2-(2-amino-4-hydroxy-5,6,7,8-tetrahydropyrido[2,3-d]pyrimidin-6-yl)ethyl]benzoyl)-L-glutamic acid.

TABLE 1

Inhibition of Dihydrofolate Reductase (DHFR)
(Kaufman et al., "Methods in Enzymology",
Jacobs and Wilcheck, Eds., Academic Press:
New York, 1974, pp 272-281)

| Compound | IC$_{50}$M |
|---|---|
| 1 | $4.3 \times 10^{-8}$ |
| 2 | $4.9 \times 10^{-5}$ |
| 3 | $7.1 \times 10^{-8}$ |
| 4 | $5.6 \times 10^{-4}$ |

TABLE 2

Inhibition of Thymidylate Synthetase
(Wahba et al., J. Biol. Chem., 1961, 236, p 611)

| Compound | IC$_{50}$M |
|---|---|
| 1 | $9.2 \times 10^{-5}$ |
| 2 | $7.7 \times 10^{-5}$ |
| 3 | $9.2 \times 10^{-4}$ |
| 4 | $>1 \times 10^{-3}$ |

TABLE 3

Substrate for Folate Polyglutamate Synthetase
Incubation with partially purified mouse liver
FPGS [specific activity = 1.2 nmol h$^{-1}$ (mg of protein)]
for one hour at 37° C.; full saturation curves obtained
for duplicate assays at 6 concentrations - see Moran et
al., Anal. Biochem., 1984, 146, 326.

| Compound | Rel* K$_m$ | Rel* V$_{max}$ |
|---|---|---|
| 1 | 0.86 ± 0.11 | 0.35 ± 0.02 |
| 2 | 0.68 ± 0.14 | 0.90 ± 0.10 |
| 3 | 0.23 ± 0.01 | 1.61 ± 0.05 |
| 4 | 0.05 ± 0.02 | 1.24 ± 0.10 |

TABLE 3-continued

Substrate for Folate Polyglutamate Synthetase
Incubation with partially purified mouse liver
FPGS [specific activity = 1.2 nmol h$^{-1}$ (mg of protein)]
for one hour at 37° C.; full saturation curves obtained
for duplicate assays at 6 concentrations - see Moran et
al., Anal. Biochem., 1984, 146, 326.

| Compound | Rel* K$_m$ | Rel* V$_{max}$ |
|---|---|---|
| FH$_4$ | 0.05 ± 0.01 | 1.31 ± 0.07 |

*Relative to folic acid.
Published data, see Moran et al., Biochemistry, 1984, 23, 4580.

TABLE 4

Inhibition of L1210 murine leukemic cells in
tissue culture - see Foley et al., Biochem. Pharmacol.,
1967, 16, 658.

| Compound | IC$_{50}$M |
|---|---|
| 1 | $1.7 \times 10^{-8}$ |
| 2 | $>10^{-4}$ |
| 3 | $3.3 \times 10^{-9}$ |
| 4 | $5.9 \times 10^{-8}$ |

TABLE 5

Increase in life span (ILS) in mice (BDF$_1$)
following peritoneal injection of 10$^{-5}$ L1210 leukemia
cells. Compounds administered intraperitoneally for 9
days at indicated dosage.

| Compound | Dose (mg/kg) | % ILS |
|---|---|---|
| 1 | 4 | 130 |
| 3 | 1 | 111 |
| 4 | 2 | 27 |
|   | 4 | 35 |
|   | 8 | 59 |
|   | 12 | 63 |

N-(4-[2-(2-amino-4-hydroxy-5,6,7,8-tetrahydropyrido[2,3-d]pyrimidin-6-yl)-ethyl]benzoyl)-L-glutamic acid in particular is a unique antimetabolite. While maintaining good activity against L-1210 leukemia which is comparable to methotrexate, the compound is a weak inhibitor of dihydrofolate reductase, indicating probable activity against the folate-related enzyme targets other than DHFR. This conclusion is supported by its activity against methotrexate-resistant cells.

TABLE 6

Effect on Methotrexate-Resistant L-1210 Leukemia

| Compound | Dose (mg/kg) | Mean Increased Life span in days |
|---|---|---|
| control | — | 0 |
| Methotrexate | 2 | 0 |
| 4 | 2 | +8 |
| 4 | 4 | +11 |
| 4 | 8 | +17 |
| 4 | 12 | +25 |

The compounds can be prepared by hydrolysis or hydrogenolysis of a glutamic acid derivative of the formula:

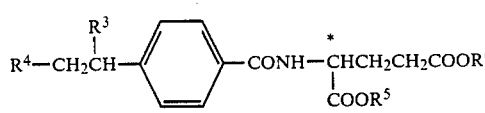

II in which $R^4$ is $R^1$ and $R^3$ are as previously defined;

R⁴ is

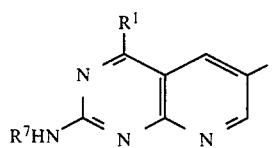

or

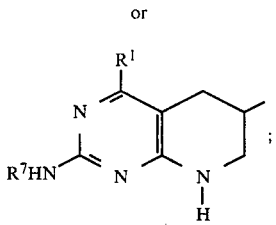

R⁵ and R⁶ are the same or different carboxylic acid protecting group; and

R⁷ is hydrogen or an amino acid protecting group.

The hydrolysis is conducted at normal temperatures utilizing aqueous acid or base, such as for example, an aqueous alkali metal hydroxide, optionally in the presence of a water miscible organic solvent such as methanol, ethanol, tetrahydrofuran, dimethylformamide, and the like, or an acid, as for example trifluoroacetic acid. When base is used, the product is initially formed as the dicationic glutamate salt and can be readily precipitated by adjustment of pH, as through acidification with, for example, acetic acid. The resulting products generally are high melting crystalline or microcrystalline solids.

The glutamic acid intermediate of Formula II can be obtained by hydrogenating a pyrido[2,3-d]pyrimidine compound of the formula:

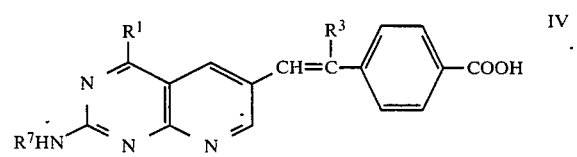

wherein R¹, R³, R⁵, R⁶ and R⁷ are as previously defined. The hydrogenation can be performed at from 50 to 100 psi in an inert solvent and in the presence of a suitable catalyst such as the noble metals or metal oxides such as palladium or platinum oxide, optionally on a support such as carbon or calcium carbonate; e.g. Pd/C, Pd/CaCO₃, PtO₂.

The 5,6,7,8-tetrahydropyrido[2,3-d]pyrimidinyl intermediate of Formula II in which R⁴ is

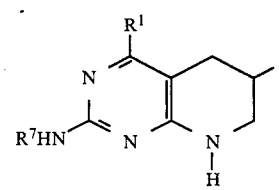

can be produced by independent hydrogenation of the corresponding compound of Formula II wherein R⁴ is

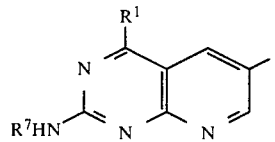

Alternatively, a 5,6,7,8-tetrahydropyrido[2,3-d]pyrimidinyl intermediate of Formula II can be formed directly in the hydrogenation of the pyrido[2,3-d]pyrimidine intermediate of Formula III through the use of more vigorous conditions, such as increasing the hydrogenation time, increasing the pressure and/or raising the temperature.

The intermediate of Formula III can be prepared in several ways. In one embodiment, a benzoic acid derivative

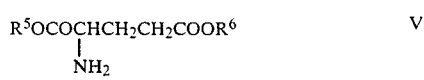

is coupled with a protected glutamic acid derivative of the formula $$R^5OCOCHCH_2CH_2COOR^6 \quad\quad V$$
$$|$$
$$NH_2$$

utilizing conventional condensation techniques for forming peptide bonds, such as activation of the carboxylic acid through formation of the mixed anhydride, treatment with DCC, or use of diphenylchlorophosphonate.

Alternatively an aldehyde of the formula

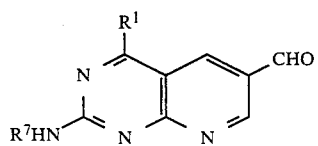

(see Taylor et al., J. Org. Chem, 1983, 48, 4852) can be coupled with a Wittig reagent of the formula

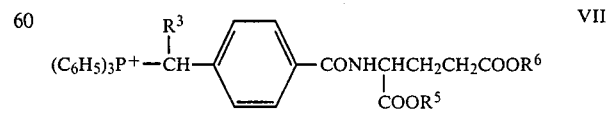

(see Yan, J. Het. Chem., 1979, 16, 541) in the presence of sodium hydride, or another strong non-nucleophilic base, in a solvent such as N-methylpyrrolidone or dimethylformamide. The reverse reaction also can be employed, namely the reaction of a Wittig reagent of the formula

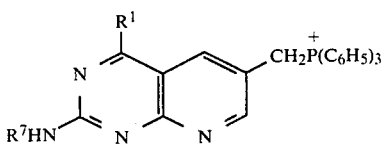

with a N-(4-formyl- or 4-alkanoylbenzoyl)-L-glutamic acid in which the carboxylic acid groups are protected.

The benzoic acid derivative of Formula IV can be prepared by cyclization of a 4-[1-(2-substituted 3-cyano-pyridin-5-yl)alk-1-en-2-yl]benzoate of the formula

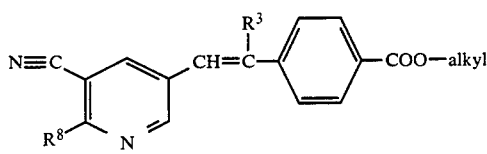

in which $R^8$ is amino or 4-nitrophenylthio, with guanidine in t-butanol and an equimolar amount of an alkali metal t-butoxide such as sodium or potassium t-butoxide. Generally, the benzoate ester is a t-butyl ester. Other alkoxide-alcohol combinations can also be used for the guanidine cyclization reaction, but care should be taken to minimize transesterification. The product of this cyclization is a 4-[1-(2,4-diaminopyrido[2,3-d]pyrimidin-6-yl)alk-en-2-yl]benzoate of the formula

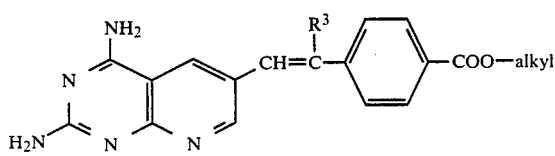

The benzoate of Formula X can be hydrolyzed with acid such as aqueous formic acid to yield the corresponding benzoic acid derivative of Formula IV in which $R^1$ is amino and $R^7$ is hydrogen. The 2,4-diamino compounds of Formula IV are converted to the corresponding 2-amino-4-hydroxy compound through treatment with base. It is desirable first to protect the 2-amino group through conversion to the acetamido group. Hence treatment with acetic anhydride in the presence of a hydrogen acceptor such as 4-dimethylaminopyridine results in acylation of the 2-amino group and formation of a benzoic acid mixed anhydride, the latter being hydrolyzed with base to regenerate the free benzoic acid derivative of Formula IV. Treatment with base such as 1N sodium hydroxide then generates the corresponding 4-hydroxy compound.

Intermediate IX also can be prepared through use of a Wittig reagent. Thus [2-(4-nitrophenylthio)-3-cyanopyridin-5-ylmethyl]triphenylmethylphosphonium bromide can be obtained according to Taylor et al., J. Org. Chem., 1983, 48, 4852 by condensation of 2-methyl-3-ethoxyacrolein and alpha-cyanothioacetamide to yield 3-cyano-5-methyl-2(1H)pyridinethione, treatment of the product with 4-nitrofluorobenzene to yield 2-(4-nitrophenylthio)-3-cyano-5-methylpyridine, bromination with N-bromosuccinimide to yield 2-(4-nitrophenylthio)-3-cyano-5-bromomethylpyridine, and addition of triphenylphosphine. This compound is then coupled with a compound of the formula

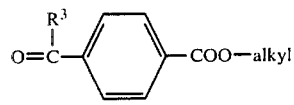

in which $R^3$ is as previously defined.

Amino and carboxylic acid protecting groups are described for example by Greene in "Protective Groups in Organic Synthesis", John Wiley & Sons, Inc., 1981, and McOmie in "Protective Groups in Organic Chemistry", Plenum Press, 1983.

The compounds of Formula IA and IB can be used, alone or in combination, to treat neoplasms which in the past have been treated with methotrexate, including choriocarcinoma, leukemia, adenocarcinoma of the female breast, epidermid cancers of the head and neck, squamous or small-cell lung cancer, and various lymphosarcomas. The compounds can also be used to treat mycosis fungoides and psoriasis which are responsive to methotrexate.

The compounds may be administered either orally or preferably parenterally, alone or in combination with other anti-neoplastic agents, steroids, etc., to a mammal suffering from neoplasm and in need of treatment. Parenteral routes of administration include intramuscular, intrathecal, intravenous or intraarterial. In general, the drug is administered in much the same fashion as methotrexate, but because of its different mode of action N-(4-[2-(2-amino-4-hydroxy-5,6,7,8-tetrahydropyrido[2,3-d]pyrimidin-6-yl)ethyl]-benzoyl)-L-glutamic acid can be administered in higher dosages than those usually employed with methotrexate Leucovorin rescue is not needed. Dosage regimens must be titrated to the particular neoplasm, the condition of the patient, and the response but generally doses will be from about 10 to about 100 mg/day for 5–10 days or single daily administration of 250–500 mg, repeated periodically; e.g. every 14 days. Oral dosage forms include tablets and capsules containing from 1–10 mg of drug per unit dosage. Isotonic saline solutions containing 20–100 mg/ml can be used for parenteral administration.

The following examples will serve to further illustrate the invention. In the NMR data, "s" denotes singlet, "d" denotes doublet, "t" denotes triplet, "q" denotes quartet, "m" denotes multiplet, and "br" denotes a broad peak.

EXAMPLE 1

[3-Cyano-2-(4-nitrophenylthio)-5-pyridinylmethyl]triphenylphosphonium Bromide

A. A mixture of 60.00 g (0.221 mol) of 3-cyano-2-(4-nitrophenylthio)-5-methylpyridine, 39.37 g (0.221 mol) of N-bromosuccinimide, 3.0 g of benzoyl peroxide and 60 mL of benzene was refluxed for 16 hours while being irradiated with a 275-W sunlamp. The solvent was removed under reduced pressure and the residue was shaken with a mixture of 1 L of water and 1 L of methylene chloride. The organic layer was separated, washed with 1 L of water, dried over anhydrous magnesium sulfate, and filtered. Removal of the solvent by evaporation under reduced pressure yielded 3-cyano-2-(4-nitrophenylthio)-5-bromomethylpyridine which can be used in the following step without further purification.

B. The solid obtained in Part A was stirred at room temperature with a solution of 58.01 g (0.221 mol) of triphenylphosphine in 500 mL of benzene. Filtration of the reaction mixture gave 77.63 g of [3-cyano-2-(4-nitrophenylthio)-5-pyridinylmethyl]triphenylphosphonium bromide.

Stirring of the mother liquor at room temperature for 6 hours afforded an additional 5.67 g, (total yield 83.30 g, 62%). Recrystallization from acetonitrile gave [3-cyano-2-(4-nitrophenylthio)-5-pyridinylmethyl]triphenylphosphonium bromide as light yellow crystals, mp <200° C., with resolidification, mp 253°–256° C. with dec.

C. Alternatively, 3-cyano-2-(4-nitrophenylthio)-5-bromomethylpyridine is allowed to react in tetrahydrofuran with tri-(n-butyl)phosphine for ten hours. Following the addition of ether, the solid which forms is collected by filtration and washed with 1:1 tetrahydrofuran:ether to yield [3-cyano-2-(4-nitrophenylthio)-pyridin-5-ylmethyl]-tri-(n-butyl)phosphonium bromide as a white solid; mp 175°–176° C.; NMR (CDCl$_3$, 80 MHz) d 0.85–2.63 (m, 27H), 4.76 (d, 2H, J=15.4 Hz), 7.74 (d, 2H, J=9.0 Hz), 8.26 (d, 2H, J=9.0 Hz), 8.55 (brs, 1H), 8.79 (brs, 1H); IR (KBr) 2950, 2860, 2220, 1595, 1575, 1515, 1390, 1340, 1075 and 845 cm$^{-1}$; HRMS 471.2116 (M$^+$-HBr), Calc'd. for C$_{25}$H$_{34}$N$_3$O$_2$PS 471.2109.

EXAMPLE 2

3-Cyano-2-(4-nitrophenylthio)-5-[2-(4-ethoxycarbonylphenyl)ethenyl]pyridine

A. A mixture of 4.544 g (7.42 mmol) of [3-cyano-2-(4-nitrophenylthio)-5-pyridinylmethyl]triphenylphosphonium bromide, 0.751 g (7.42 mmol) of triethylamine and 50 mL of chloroform was stirred at room temperature for 15 minutes and 1.322 g (7.42 mmol) of 4-ethoxycarbonylbenzaldehyde then were added. After stirring at room temperature for 96 hours, 100 mL of water were added, the mixture was filtered, and the organic layer was separated and washed twice with 100 mL portions of water, dried and filtered. Evaporation of the filtrate under reduced pressure gave a residue which was chromatographed on silica gel. Unreacted aldehyde was eluted with 2:1 petroleum ether:benzene, while the title compound, alternatively named as 2-(4-nitrophenylthio)-3-cyano-5-(4-ethoxycarbonylstyryl)-pyridine, was eluted with benzene. Evaporation of the benzene eluate gave 2.82 g (88%) of 3-cyano-2-(4-nitrophenylthio)-5-[2-(4-ethoxycarbonylphenyl)ethenyl]-pyridine as a light yellow solid. The product turns from a solid to a gum below 100° C. and then to a clear liquid between 180° and 220° C.; NMR (Me$_2$SO-d$_6$) delta 1.34 (t, 3H, J=6.3 Hz), 4.32 (q, 2H, J-6.3 Hz), 6.73 (d, 1H, J=13 Hz), 6.99 (d, 1H, J=13 Hz), 7.27 (d, 2H, J=9 Hz), 7.74, 7.85, 7.94 (dd, 2H, 2H), 8.26, 8.31 (dd, 2H, 1H), 8.38 (d, 1H, J=1.8 Hz); IR (KBr) 2220, 1707, 1605, 1597, 1575, 1512, 1344, 1295–1277, 1174 cm$^{-1}$.

Anal.: Calc'd. for C$_{23}$H$_{17}$N$_3$O$_4$S: C, 64.08; H, 3.97; N, 9.74; S, 7.43. Found: C, 63.82; H, 4.01; N, 9.51; S, 7.38.

B. 3-Cyano-2-(4-nitrophenylthio)-5-[2-(4-tert-butoxycarbonylphenyl)ethenyl]pyridine was prepared in 81% yield by the above method utilizing however 4-(tert-butoxycarbonyl)benzaldehyde in place of 4-ethoxycarbonylbenzaldehyde; mp indefinite (cis-trans mixture); NMR (CDCl$_3$) delta 1.62 (s, 9H), 6.43 (d, 1H, J=13 Hz), 6.90 (d, 1H, J=13 Hz), 7.24 (d, 2H, J=9 Hz), 7.69 (d, 2H, J=8.1 Hz), 7.76 (d, 1H, J=2.7 Hz), 7.92 (d, 2H, J=8.1 Hz), 8.22 (d, 2H, J=9 Hz), 8.34 (d, 1H, J=2.7 Hz); IR (KBr) 2220, 1707, 1600, 1577, 1518, 1341, 1290, 1163 cm$^{-1}$.

Anal.: Calc'd. for C$_{25}$H$_{21}$N$_3$O$_4$S: C, 65.35; H, 4.61; N, 9.14; S, 6.98. Found: C, 65.28; H, 4.68; N, 9.20; S, 6.93.

In a similar fashion by substituting a 4-alkoxycarbonylacetophenone or a 4-alkoxycarbonylpropiophenone for 4-ethoxycarbonylbenzaldehyde, there is respectively obtained the corresponding 3-cyano-2-(4-nitrophenylthio)-5-[2-(4-alkoxycarbonylphenyl)prop-1-enyl]pyridine and 3-cyano-2-(4-nitrophenylthio)-5-[2-(4-alkoxycarbonylphenyl))but-1-enyl]pyridine compounds. This can be exemplified as follows:

To a solution of 18.89 g of [3-cyano-2-(4-nitrophenylthio)-5-pyridinylmethyl]-tri-(n-butyl)phosphonium bromide in 150 mL of dry methylene chloride were added in several small portions 5.36 mL of 1,5-diazabicyclo[5.4.0]undec-5-ene. After stirring the reaction mixture under a nitrogen atmosphere for 15 minutes, 7.53 g of 4-(t-butoxycarbonyl)acetophenone (alternatively named as tert-butyl 4-acetylbenzoate) were added. The mixture was heated under reflux for 72 hours, cooled to room temperature, and extracted with a saturated sodium chloride solution. The extracts were dried over anhydrous sodium sulfate and then chromatographed on flash silica gel using methylene chloride as the eluent. The eluate was concentrated under reduced pressure and the residue was triturated with ether. The resulting solid was collected by filtration to yield 5.64 g (35%) of trans-3-cyano-2-[(4-nitrophenylthio)]-5-[2-(4-tert-butoxycarbonylphenyl)prop-1-enyl]pyridine as a pale yellowish solid: mp 180°–181.5° C. (benzene-ether); NMR (CDCl$_3$, 250 MHz) d 1.61 (s, 9H), 2.29 (d, 3H, J=1.23 Hz), 6.70 (brs, 1H), 7.52 (d, 1H, J=8.62 Hz), 7.74 (d, 1H, J=8.84 Hz), 7.92 (d, 1H, J=2.09 Hz), 8.00 (d, 1H, J=8.62 Hz), 8.27 (d, 1H, J=8.84 Hz), 8.53 (d, 1H, J=2.09 Hz); IR (KBr) 3060, 2970, 2220, 1695, 1595, 1515, 1425, 1380, 1365, 1340, 1290, 1160, 1110, 1010 and 840 cm$^{-1}$.

Anal. Calc'd. for C$_{26}$H$_{23}$N$_3$O$_4$S: C, 65.94; H, 4.90; N, 8.87; S, 6.77. Found: C, 66.88; H, 4.64; N, 8.51; S, 6.77.

Concentration of the filtrate under reduced pressure and trituration of the residue, followed by filtration and washing with ether, yielded 2.08 g (13%) of the cis-3-cyano-2-(4-nitrophenylthio)-5-[2-(4-tert-butoxycarbonylphenyl)prop-1-enyl]pyridine as a pale yellowish solid, mp 126°–127° C. (ethyl acetate-hexane); NMR (CDCl$_3$, 250 MHz) d 1.60 (s, 9H), 2.25 (d, 3H, J=1.41 Hz), 6.39 (brs), 7.18 (d, 1H, J=8.28 Hz), 7.41 (d, 1H, J=2.22 Hz), 7.63 (d, 1H, J=8.91 Hz), 7.95 (d, 1H, J=8.28 Hz), 8.09 (d, 1H, J=2.22 Hz), 8.23 (d, 1H, J=8.91 Hz); IR (KBr) 3110, 2970, 2225, 1720, 1520, 1345, 1165, 1105, 920 and 840 cm$^{-1}$.

Anal. Calc'd. for C$_{26}$H$_{23}$N$_3$O$_4$S: C, 65.94; H, 4.90; N, 8.87; S, 6.77. Found: C, 65.92; H, 4.81; N, 8.62; S, 656.

The 4-(t-butoxycarbonyl)acetophenone utilized in the foregoing procedure can be prepared as follows:

To a suspension of 1.64 g of 4-acetylbenzoic acid in 30 mL of dry benzene were added 3.0 mL of freshly distilled thionyl chloride. The mixture was heated under reflux for 5 hours. The reaction mixture was cooled to room temperature and the solvent was removed under reduced pressure. The resulting residue was dissolved in 5 mL of dry methylene chloride and the solution was added to a mixture of 1.11 g of dry tert-butanol and 1.42 g of dry pyridine. After stirring the reaction mixture under a nitrogen atmosphere for 15 hours, the mixture was diluted with methylene chloride and extracted with water. The organic solution was dried over anhydrous sodium sulfate and the solvent was removed under reduced pressure. The residue was chromatographed on a column of silica gel using a 20% ethyl acetate-hexane mixture as the eluent. The major fraction isolated from the column contained 2.01 g (91%) of 4-(t-butoxycarbonyl)acetophenone as a white solid: mp 56.5°–57.5° C.; NMR (CDCl$_3$ 80 MHz) d 1.61 (s, 9H), 2.63 (s, 3H, 7.95 (d, 2H, J=9.0 Hz), 8.09 (d, 2H, J=9.0 Hz); IR (KBr) 2980, 2930, 1720, 1680, 1400, 1365, 1295, 1250, 1165, 1100, 845, 760 and 690 cm$^{-1}$.

Alternatively, 4-(t-butoxycarbonyl)acetophenone can be isolated by distillation under reduced pressure, bp 90°–100° C./0.1 mm. Analogously 4-(t-butoxycarbonyl)propiophenone is prepared and converted to 3-cyano-2-(4-nitrophenylthio)-5-[2-(4-tert-butoxycarbonylphenyl)but-1-enyl]pyridine.

EXAMPLE 3

2-Amino-3-cyano-5-[2-(4-ethoxycarbonylphenyl)ethenyl]pyridine

A suspension of 2.00 g (4.64 mmol) of 3-cyano-2-(4-nitrophenylthio)-5-[2-(4-ethoxycarbonylphenyl)ethenyl]pyridine, 1.553 g (6.95 mmol) of cupric bromide, and 50 mL of liquid ammonia was stirred in a pressure tube at room temperature for 13 days. Evaporation of the ammonia afforded a dark residue which was chromatographed over magnesium silicate using methylene chloride as eluant. The eluate was removed by evaporation under reduced pressure and the residue chromatographed on silica gel. Unreacted starting material was eluted with benzene while 0.87 g (64%) of the product, which can be alternatively named as 2-amino-3-cyano-5-(4-ethoxycarbonylstyryl)pyridine, was eluted with ethyl acetate and obtained by evaporation of the ethyl acetate solvent as a light yellow solid, mp 135°–141.5° C.; NMR (Me$_2$SO-d$_6$) delta 1.39 (t, 3H, J-6.3 Hz), 4.38 (q, 2H, J=6.3 Hz), 6.67 (m, 2H), 7.10 (br, 2H), 7.45 (d, 2H, J=9 Hz), 7.71 (d, 1H, J=3.6 Hz), 7.97 (d, 2H, J=9 Hz), 8.11 (d, 1H, J=3.6 Hz); IR (KBr) 3155, 2218, 1715, 1650–1645, 1593, 1491, 1277, 1100 cm$^{-1}$.

Anal. Calc'd. for C$_{17}$H$_{15}$H$_3$O$_2$: C, 69.61; H, 5.16; N, 14.33. Found: C, 69.37; H, 5.25; N, 14.22.

By substituting an equivalent amount of 3-cyano-2-(4-nitrophenylthio)-5-[2-(4-tert-butoxycarbonylphenyl)ethenyl]pyridine in the foregoing procedure there is obtained 2-amino-3-cyano-5-[2-(4-tert-butoxycarbonylphenyl)ethenyl]pyridine, which can be alternatively named as 2-amino-3-cyano-5-(4-t-butoxycarbonylstyryl)pyridine; yield 1.14 g (84%) of light yellow crystals, mp 190°–195° C.; NMR (Me$_2$SO-d$_6$) delta 1.57 (s, 9H), 6.57–6.60 (m, 2H), 7.00 (br, 2H), 7.35 (d, 2H, J=8.1 Hz), 7.65 (d, 1H, J=2.7 Hz), 7.84 (d, 2H, J=8.1 Hz), 8.00 (d, 1H, J=2.7 Hz); IR (KBr) 3460, 3360, 2215, 1707, 1623, 1480, 1300, 1287, 1158 cm$^{-1}$.

Anal. Calc'd. for C$_{19}$H$_{19}$N$_3$O$_2$: C, 71.00; H, 5.96; N, 13.07. Found: C, 70.83; H, 6.03; N, 12.83.

EXAMPLE 4

2,4-Diamino-6-[2-(4-tert-butoxycarbonylphenyl)ethenyl]pyrido[2,3-d]pyrimidine

To a solution of 4.54 mmol of guanidine as the free base (obtained from 0.433 g (4.54 mmol) of guanidine hydrochloride and 0.114 g of sodium in 25 mL of dry tert-butanol) was added 1.325 g (4.12 mmol) of 2-amino-3-cyano-5-[2-(4-tert-butoxyphenyl)ethenyl]pyridine. The deep red suspension was heated at reflux under dry nitrogen for 8 hours. The reaction mixture was cooled to room temperature and filtered. The precipitate was washed successively with water, acetone, and ether and was then dried under reduced pressure to yield 0.911 g (61%) of the title compound, which can be alternatively named as 2,4-diamino-6-(4-tert-butoxycarbonylstyryl)-5-deazapteridine, as a light yellow solid, mp >350° C.; NMR (Me$_2$SO-d$_6$) delta 1.55 (s, 9H), 6.42 (br, 2H), 6.73 (m, 2H), 7.30–8.00 (br, 2H), 7.35 (d, 2H, J=9 Hz), 7.81 (d, 2H, J=9 Hz), 8.34 (m, 2H); IR (KBr) 3320–3300, 3200–3140, 2970, 1718, 1626, 1610–1600, 1550, 1450–1445, 1288, 1167, 812 cm$^{-1}$.

Anal.: Calc'd. for C$_{20}$H$_{21}$N$_5$O$_2$: C, 66.10; H, 5.82; N, 19.27. Found: C, 65.88; H, 5.86; N, 18.98.

EXAMPLE 5

2,4-Diamino-6-[2-(4-carboxyphenyl)ethenyl]pyrido[2,3-d]pyrimidine

A. A solution of 1.27 g of 2,4-diamino-6-[2-(4-tert-butoxycarbonylphenyl)ethenyl]pyrido[2,3-d]pyrimidine and 10 mL 88% formic acid was stirred at room temperature. A yellow solid started to form after about 12 hours and after 4 days of stirring, the reaction mixture was filtered. The collected solid was washed well successively with water, methanol, and acetone and was then dried under reduced pressure to give 0.85 g (79%) of the title compound, which can be alternatively named as 2,4-diamino-6-(4-carboxystyryl)-5-deazapteridine, mp >300° C.

B. Alternatively, 0.48 g of 2,4-diamino-6-[2-(4-tert-butoxycarbonylphenyl)ethenyl]pyrido[2,3-d]pyrimidine was added to a saturated solution of hydrogen chloride in 20 mL of nitromethane at 0°. The reaction mixture quickly became viscous and turned a deep yellow color and after a few minutes of stirring, a granular solid formed. After 1 hour of stirring, 50 mL of ether were added and the precipitate was collected by filtration. The collected solid was dissolved in 50 mL of 10% aqueous sodium carbonate. Acidification with acetic acid then resulted in the separation of a yellow solid which was collected by filtration and dried under reduced pressure; yield 0.31 g (92%) of 2,4-diamino-6-[2-(4-carboxyphenyl)ethenyl]pyrido[2,3-d]pyrimidine; NMR (Me$_2$SO-d$_6$) delta 6.75 (s, 2H), 7.35, 7.85 (AB q, 4H, J=9 Hz), 8.38 (s, 2H); IR (Nujol) 3400–2300, 3380, 3150, 1700, 1650, 1630, 1590 cm$^{-1}$.

EXAMPLE 6

2,4-Diamino-6-[2-(4-tert-butoxycarbonylphenyl)prop-1-enyl]pyrido[2,3-d]pyrimidine To a suspension containing 1.93 g of guanidine hydrochloride in 75 mL of dry tert-butanol at 50° C. under a nitrogen atmosphere was added 0.50 g of sodium metal. After all the sodium was dissolved, 7.97 g of trans-3-cyano-2-(4-nitrophenylthio)-5-[2-(4-tert-butoxycarbonylphenyl)prop-1-enyl]pyridine was added. The mixture was heated under reflux for 3 hours, cooled to room temperature, diluted with ether, and filtered. The solid was washed with water and acetone, and then dried under reduced pressure to yield 4.66 g (73%) of the title compound as a pale yellowish solid; mp >300° C.; NMR (DMSO-d$_6$, 80 MHz) d 1.56 (s, 9H), 2.23 and 2.29 (brs, 3H), 6.57 and 6.99 (brs, 1H), 7.25–8.73 (m, 8H); IR (KBr) 3340, 3130, 1710, 1640, 1608, 1540, 1450, 1365, 1340, 1290, 1165, 1110, 840 and 810 cm$^{-1}$.

EXAMPLE 7

2,4-Diamino-6-[2-(4-carboxyphenyl)prop-1-enyl]-pyrido[2,3-d]pyrimidine

A suspension containing 4.58 g of 2,4-diamino-6-[2-(4-tert-butoxycarbonylphenyl)prop-1-enyl]pyrido[2,3-d]pyrimidine in 200 mL of a saturated solution of hydrogen chloride gas in nitromethane was stirred at 0° C. for 1 hour, and then at room temperature for 3 hours. After dilution with ether, the reaction mixture was filtered and the collected solid was washed successively with water, methanol, and acetone and then dried under reduced pressure to give 3.90 g (100%) of 2,4-diamino-6-[2-(4-carboxyphenyl)prop-1-enyl]pyrido[2,3-d]pyrimidine. NMR (DMSO-$d_6$, 80 MHz) d 2.31 (brs, 3H), 6.77 and 7.07 (brs, 1H), 7.74 (d, 2H, J=8.5 Hz), 7.98 (d, 2H, J=8.5 Hz), 8.26, (d, 1H, J=2.0 Hz), 8.74 d, 1H, J=2.0 Hz).

EXAMPLE 8

2-Amino-4-hydroxy-6-[2-(4-carboxyphenyl)ethenyl]-pyrido[2,3-d]pyrimidine

A. A suspension of 1.0 g of 2,4-diamino-6-[2-(4-carboxyphenyl)ethenyl]pyrido[2,3-d]pyrimidine in 30 mL of 1N aqueous sodium hydroxide was heated under reflux under nitrogen for 3 hours. The resulting homogeneous orange solution was cooled to room temperature, acidified with 6 mL of glacial acetic acid, and the resulting yellow precipitate collected by filtration. The filter cake was washed successively with water, methanol, acetone and ether and was then dried under reduced pressure to give 0.88 g (88%) of the title compound, which can be alternatively named as either 6-[2-(4-carboxyphenyl)ethenyl]-5-deazapterin or 6-(4-carboxystyryl)-5-deazapterin, as a microcrystalline yellow powder, mp >250° C.; NMR (TFA-$d_1$ delta 6.8, 7.25 (AB q, 2H, J=12 Hz), 7.45, 8.2 (AB q, 4H, J=9 Hz), 8.55 (s, 1H), 8.85 (s, 1H); IR (Nujol) 3500–2500 (br), 1670, 1625, 1600 cm$^{-1}$.

B. In a similar fashion, 2,4-diamino-6-[2-(4-carboxyphenyl)prop-1-enyl]pyrido[2,3-d]pyrimidine is converted to 2-amino-4-hydroxy-6-[2-(4-carboxyphenyl)-prop-1-enyl]pyrimidine, mp >250° C.; NMR (DMSO-$d_6$, 80 MHz) d 2.28 and 2.30 (brs, 3H), 6.77 and 7.06 (brs, 1H), 7.72 (d, 2H, J=8.5 Hz), 7.97 (d, 2H, J=8.5 Hz), 8.27 (d, 1H, J=2.0 Hz), 8.72 (d, 1H, J=2.0 Hz).

EXAMPLE 9

2-Acetamido-4-hydroxy-6-[2-(4-acetoxycarbonyl-phenyl)ethenyl]pyrido[2,3-d]pyrimidine A suspension of 0.88 g of 2-amino-4-hydroxy-6-[2-(4-carboxyphenyl)ethenyl]pyrido[2,3-d]pyrimidine in 20 mL of acetic anhydride containing 0.05 g of 4-dimethylaminopyridine was heated under nitrogen at 120° C. for 3 hours. The reaction mixture was cooled to room temperature. Fifty milliliters of ether were added and the resulting yellow solid was collected by filtration to yield 0.95 g (84%) of the title compound; mp >300° C.; IR (Nujol) 3350, 3150, 1800, 1670, 1600 cm$^{-1}$.

EXAMPLE 10

2-Acetamido-4-hydroxy-6-[2-(4-carboxyphenyl)ethenyl]pyrido[2,3-d]pyrimidine

To a suspension of 0.95 g of 2-acetamido-4-hydroxy-6-[2-(4-acetoxycarbonylphenyl)ethenyl]pyrido[2,3-d]pyrimidine in 50 mL of water was added 1N aqueous sodium hydroxide until a homogenous solution was obtained. Acidification with acetic acid resulted in the formation of a yellow precipitate which was collected by filtration. The filter cake was washed sequentially with water, methanol, acetone and ether. The residual solid was recrystallized from DMF to give 0.65 g (77%) of the title compound, which can be alternatively named as 2-acetamido-6-(4-carboxystyryl)-5-deaza-4(3H)-pteridinone, as a microcrystalline yellow solid, mp >300° C.; NMR (TFA-$d_1$) delta 2.5 (s, 3H), 6.85, 7.32 (AB q, 2H, J=12 Hz), 7.45, 8.18 (AB q, 4H, J=9 Hz), 8.65 (s, 1H), 9.02 (s, 1H); IR (Nujol) 3300–2200 (br), 1685, 1655, 1630, 1600, 1565 cm$^{-1}$. MS: Calc'd. for $C_{18}H_{14}N_4O_4$: 350. Found: m/e 350 (base), 308.

EXAMPLE 11

2-Acetamido-4-hydroxy-6-[2-(4-carboxyphenyl)prop-1-enyl]pyrido[2,3-d]pyrimidine

By subjecting 2-amino-4-hydroxy-6-[2-(4-carboxyphenyl)prop-1-enyl]pyrido[2,3-d]pyrimidine to the procedures of Examples 9 and 10, there was obtained 2-acetamido-4-hydroxy-6-[2-(4-carboxyphenyl)prop-1-enyl]pyrido[2,3-d]pyrimidine, mp >250° C.; in an overall yield of 45%; NMR (CF$_3$CO$_2$D/DMSO-$d_6$, 80 mHz) d 2.15 (s, 3H), 2.22 (s, 3H), 6.72 (brs, 1H), 7.45 (d, 2H, J=8.4 Hz), 7.92 (d, 2H, J=8.4 Hz), 8.65 (d, 1H, J=2.0 Hz), 8.98 (d, 1H, J=2.0 Hz).

EXAMPLE 12

Diethyl N-(4-[2-(2,4-diaminopyrido[2,3-d]pyrimidin-6-yl)ethenyl]benzoyl)-L-glutamate A. To a solution of 1.0 g (0.0033 mol) of 2,4-diamino-6-[2-(4-carboxyphenyl)ethenyl]pyrido[2,3-d]pyrimidine and 1 g of N-methylmorpholine in 120 mL of N-methylpyrrolidone cooled to 5° C. is added, in a dropwise fashion, 1.4 g (0.0048 mol) of diphenyl chlorophosphonate. The reaction mixture was stirred for 1 hour and an additional 0.5 mL of N-methylmorpholine were added, followed by 1.1 g (0.0048 mol) of diethyl L-glutamate hydrochloride. The reaction mixture was stirred overnight at room temperature and the solvent then was removed under reduced pressure. The residual solid was washed with 50 mL of dry ether, triturated with 100 mL of 1N aqueous sodium hydroxide, and the resulting suspension centrifuged. The collected solid was dissolved in 200 mL of 3:1 chloroform:methanol and filtered through Florisil. The filtrate was evaporated to a small volume; 10 g of Florisil were added, and the resulting impregnated Florisil added to the top of a Florisil column which was then eluted sequentially with ethyl acetate followed by ethyl acetate containing increasing quantities of methanol (9:1, 3:1, and 1:1). The title compound was collected in the 3:1 and 1:1 fractions. Evaporation of the combined eluates gave a glassy material which was triturated with ether and then collected by filtration; yield 0.41 g (26%), mp 183°–185° C.; NMR (Me$_2$SO-$d_6$/TFA) delta 1.25–1.45 (overlapping t, 6H, J=7 Hz), 2.25–2.50 (m, 2H), 2.5–2.8 (m, 2H), 4.05–4.45 (overlapping q, 4H, J=7 Hz), 4.8–5.0 (m, 1H), 6.8, 7.2 (AB q, 2H, J=16 Hz), 7.4, 7.85 (AB q, 4H, J=9 Hz), 8.6 (s, 1H), 9.05 (s, 1H); IR (Nujol) 3500–3000, 1730, 1635, 1605 cm$^{-1}$. MS: Calc'd. for $C_{25}H_{28}N_6O_5$: 492. Found: m/e 492, 290, 94, 84.

B. Alternatively the triphenylphosphonium salt [prepared from triphenylphosphine and diethyl 4-bromoethylbenzoylglutamate (7.86 g, 0.012 mol) following the method of Yan et al., *J. Het. Chem.*, 16, 541 (1979)] was added portionwise to a slurry of 0.4 g (0.01 mol) of sodium hydride (60% suspension in oil) in 70 mL of dry N-methylpyrrolidone over a period of 10 minutes. The resulting red reaction mixture was stirred at room temperature under nitrogen for 1 hour. To this in situ Wittig reagent were added 2.27 g (0.012 mol) of 2,4-diamino-6-formylpyrido[2,3-d]pyrimidine [prepared by the method of Baldwin et al., *J. Org. Chem.* 43, 2529 (1978)]. The resulting slurry was stirred at room temperature under nitrogen for 3 weeks. The solvent was then evaporated under reduced pressure, the residual solid triturated with benzene to remove triphenylphosphine oxide, and the purified solid collected by centrifugation. The solid was resuspended in water, filtered, and the collected solid dissolved in 200 mL of chloroform:methanol (1:2). Florisil (10 g) was added, the mixture was evaporated to dryness, and the impregnated Florisil residue applied to the top of a Florisil column which was then eluted with ethyl acetate containing increasing quantities of methanol (from 9:1 to 1:1). Fractions containing eluted material were combined and were shown to contain two products (TLC). The mixture was chromatographed again on silica gel utilizing chloroform and methanol as eluants. The initial fraction was a phosphorane and the product was thereafter eluted and obtained in a yield of 1.7 g (34.5%) in form identical to that obtained in part A of this example.

C. Following the procedure of part A of this example but utilizing 2,4-diamino-6-[2-(4-carboxyphenyl)prop-1-enyl]pyrido[2,3-d]pyrimidine, there can be obtained diethyl N-(4-[1-(2,4-diaminopyrido[2,3-d]pyrimidin-6-yl)propen-2-yl]benzoyl)-L-glutamate.

Alternatively, 2.2 g (0.0074 mol) of di-tert-butyl L-glutamate hydrochloride were allowed to react with 1.5 g (0.0049 mol) of 2,4-diamino-6-[2-(4-carboxyphenyl)ethenyl]pyrido[2,3-d]pyrimidine, to yield di-tert-butyl N-(4-[2-(2,4-diaminopyrido[2,3-d]pyrimidin-6-yl)ethenyl]benzoyl)-L-glutamate in a yield of 1.3 g (48%), mp >300° C. NMR (CDCl$_3$/CD$_3$OD) delta 1.47, 1.52 (2s, 18H), 2.0–2.6 (m, 4H), 4.5–7.0 (m, 1H), 6.8 (br, s, 2H), 7.35, 7.78 (AB q, 4H, J=9 Hz), 8.38 (s, 1H), 8.5 (s, 1H); IR (Nujol) 3350, 3180, 1725, 1640, 1605 cm$^{-1}$. MS: Calc'd.: for C$_{29}$H$_{36}$N$_6$O$_5$: 548. Found: m/e 548, 446, 290.

EXAMPLE 13

Diethyl N-(4-[2-(2-acetamido-4-hydroxypyrido[2,3-d]pyrimidin-6-yl)ethenyl]benzoyl)-L-glutamate To an ice cold solution of 1.5 g (0.0043 mol) of 2-acetamido-4-hydroxy-6-[2-(4-carboxyphenyl)ethenyl]-pyrido[2,3-d]pyrimidine in 40 mL of N-methylpyrrolidone containing 1.4 mL of N-methylmorpholine was added 1.72 g (0.0064 mol) of phenyl N-phenylphosphoramidochloridate in a single portion. The resulting mixture was stirred at 0° C. for 30 minutes. Diethyl L-glutamate hydrochloride (1.53 g, 0.0064 mol) was then added and the reaction mixture was stirred at room temperature overnight. The solvent was evaporated under reduced pressure and the residual solid triturated with 50 mL of 1N aqueous sodium carbonate. The mixture was filtered and the collected solid dissolved in 20 mL of chloroform. The chloroform solution was dried over anhydrous magnesium sulfate and filtered. The filtrate was evaporated to dryness and chromatographed on silica gel. Elution with chloroform:methanol (95:5) gave 1.52 g (66%) of the title compound, which may be alternatively named as diethyl 2-acetyl-5,10-dideaza-9,10-didehydrofolate, mp >250° C.; NMR (CDCl$_3$Me$_2$SO-d$_6$) delta 1.15–1.45 (2t, 6H, J=6 Hz), 2.0–2.65 (m, 4H), 2.3 (s, 3H), 4.0–4.35 (2q, 4H, J=6 Hz), 4.5–4.75 (m, 1H), 6.7, 6.9 (AB q, 2H, J=15 Hz), 7.33, 7.84 (AB q, 4H, J=9 Hz), 8.25–8.38 (m, 2H), 8.62 (d, 1H, J=2 Hz), 11.5–12.5 (br, 2H); IR (Nujol) 3320, 3150, 1730, 1680, 1630, 1600 cm$^{-1}$.

Anal.: Calc'd. For C$_{27}$H$_{29}$N$_5$O$_7$: C, 60.56; H, 5.42; N, 13.08. Found: C, 60.26; H, 5.45; N, 12.84.

EXAMPLE 14

Diethyl N-(4-[1-(2-acetamido-4-hydroxypyrido[2,3-d]pyrimidin-6-yl)propen-2-yl]benzyl)-L-glutamate To a solution of 0.2 g of 2-acetamido-4-hydroxy-6-[2-(4-carboxyphenyl)prop-1-enyl]pyrido[2,3-d]pyrimidine in 50 mL of N-methylpyrrolidinone containing 0.18 g of N-methylmorpholine was added 0.22 g of phenyl N-phenylphosphoramidochloridate in a single portion. After stirring the mixture at room temperature for 1 hour, 0.20 g of diethyl L-glutamate was added. The reaction mixture was stirred overnight, the solvent was removed under reduced pressure and the residue was triturated with chloroform. The mixture was filtered and the filtrate was evaporated under reduced pressure. The residue was subjected to preparative thin layer chromatography on silica gel using a 5% methanol in chloroform mixture as the eluent. This gave 74.6 mg (25%) of the title compound as a pale yellowish solid; NMR (CDCl$_3$, 250 MHz) d 1.22 (t, 3H, J=7.1 Hz), 1.30 (t, 3H J=7.1 Hz), 2.11–2.57 (m, 10H), 4.14 (q, 2H, J=7.1 Hz), 4.24 (q, 2H, J=7.1 Hz), 4.75–4.83 (m, 1H), 6.86 (brs, 1H), 7.18 (brs, 1H), 7.57 (d, 2H, J=8.42 Hz), 7.84 (d, 2H, J=8.42 Hz), 8.50 (d, 1H, J=2.01 Hz), 8.96 (brs, 1H), 10.34 (brs, 1H).

EXAMPLE 15

Diethyl N-(4-[2-(2,4-diaminopyrido[2,3-d]pyrimidin-6-yl)ethyl]-benzoyl)-L-glutamate A solution of 0.9 g of diethyl N-(4-[2-(2,4-diaminopyrido[2,3-d]pyrimidin-6-yl)ethenyl]benzoyl)L-glutamate in 40 mL of trifluoroacetic acid was hydrogenated under 55 psi of hydrogen for 24 hours using 2.5 g of Pd/C as catalyst. The catalyst was removed by filtration through celite and the filtrate was evaporated. The residual solid was triturated with 30 mL of 2N aqueous sodium carbonate, followed by a water wash. The resulting solid was purified by column chromatography on silica gel. Elution with chloroform:methanol (95:5) afforded a small amount (0.2 g) of the tetrahydro derivative while subsequent elution with chloroform:methanol (1:4) gave 0.52 g (58%) of the title compound, which can be alternatively named as diethyl N-[4-[2-(2,4-diamino-5-deaza-6-pteridyl)ethyl]benzoyl]-L-glutamate; mp >200° C.; NMR (Me$_2$SO-d$_6$) delta 1.1–1.3 (2t, 6H, J=7 Hz) 1.8–2.6 (m, 4H), 3.05 (s, 4H), 3.1–3.8 (br, 5H), 3.9–4.2 (2q, 4H, J=7 Hz), 4.3–4.5 (m, 1H), 7.35, 7.85 (AB q, 4H, J=9 Hz), 8.6 (br, s, 2H): IR (Nujol) 3320, 3150, 1650 cm$^{-1}$.

EXAMPLE 16

Diethyl N-(4-[2-(2,4-diamino-5,6,7,8-tetrapyrido[2,3-d]pyrimidin-6-yl)ethyl]benzoyl)-L-glutamate By repeating the procedure of Example 15 but continuing the hydrogenation for 72 hours, the title compound, which can be alternatively named as diethyl N-(4-[2-(2,4-diamino-5-deaza-5,6,7,8-tetrahydro-6-pteridyl)ethyl]-benzoyl)-L-glutamate, was obtained as a crude product which was chromatographed on silica gel using chloroform:methanol (95:5) to give 0.42 g (31%) of the product as a colorless microcrystalline solid; mp >250° C.; NMR (Me$_2$SO-d$_6$) delta 1.6, 1.8 (2t, 6H, J=6 Hz), 1.4–3.8 (m, 13H), 4.1 (2q, 4H, J=6 Hz), 4.3–4.6 (m, 1H), 6.8 (s, 2H), 7.35, 7.85 (AB q, 4H, J=9 Hz), 8.7 (d, 1H, J=9 Hz); IR (Nujol) 3350, 3150, 1730, 1630 cm$^{-1}$. MS: Calc'd. for C$_{25}$H$_{34}$N$_6$O$_5$: 498. Found: m/e 498, 425, 178, 165 (base), 150.

EXAMPLE 17

Diethyl N-(4-[2-(2-acetamido-4-hydroxy-5,6,7,8-tetrahydropyrido[2,3-d]pyrimidin-6-yl)ethyl]benzoyl)-L-glutamate A solution of diethyl N-(4-[2-(2-acetamido-4-hydroxypyrido[2,3-d]pyrimidin-6-yl)ethenyl]benzoyl)-L-glutamate in 30 mL of trifluoroacetic acid was hydrogenated at 55 psi of hydrogen in the presence of 1.0 g of 5% Pd/C at room temperature for 14 hours. The catalyst was removed by filtration, the filtrate evaporated under reduced pressure, and the residual solid partitioned between 100 mL of chloroform and 50 ml of 2N aqueous sodium carbonate. The organic phase was separated, dried over anhydrous magnesium sulfate, and the solvent removed by evaporation to give a gum which was chromatographed on silica gel. Elution with chloroform:methanol (97:3) gave 0.25 g (56%) of diethyl N-(4-[2-(2-acetamido-4-hydroxypyrido[2,3-d]pyrimidin-6-yl)ethyl]benzoyl)-L-glutamate; mp 215°–217° C.; NMR (CDCl$_3$) delta 1.25, 1.35 (2t, 6H, J=6 Hz), 2.1–2.5 (m, 4H), 2.55 (s, 3H), 3.1 (s, 4H), 4.15, 4.25 (2q, 4H, J=6 Hz), 4.6–4.96 (m, 1H), 7.05 (s, 1H), 7.25, 7.75 (AB q, 4H, J=9 Hz), 8.35 (d, 1H, J=3 Hz), 8.77 (d, 1H, J=3 Hz); IR (Nujol) 3200, 3150, 1725, 1675, 1630, 1605 cm$^{-1}$. Anal.: Calc'd for C$_{27}$H$_{31}$N$_5$O$_7$: C, 60.32; H, 5.81; N, 13.03. Found: C, 59.98; H, 6.03; N, 12.92.

Further elution with 95:5 chloroform:methanol yielded 0.08 g (18%) of the title compound, which can be alternatively named as diethyl 2-acetyl-5,10-dideaza-5,6,7,8-tetrahydrofolate; mp >200° C.; NMR (CDCl$_3$/Me$_2$SO-d$_6$) delta 1.24, 1.28 (2t, 6H, J=6 Hz), 1.5–3.3 (m, 13H), 2.18 (s, 3H), 4.1, 4.18 (2a, 4H, J=6 Hz), 4.4–4.7 (m, 1H), 6.2 (s, 1H), 7.28, 7.85 (AB q, 4H, J=9 Hz), 8.4 (d, 1H, J=8 Hz), IR (Nujol) 3320, 3250, 1730, 1630, 1575 cm$^{-1}$. Anal.: Calc'd for C$_{27}$H$_{35}$N$_5$O$_7$: C, 59.87; H, 6.51; N, 12.93. Found: C, 59.66; H, 6.71; N, 12.77.

EXAMPLE 18

Diethyl N-(4-[1-(2-acetamido-4-hydroxy-5,6,7,8-tetrahydropyrido[2,3-d]pyrimidin-6-yl)prop-2-yl]benzoyl)-L-glutamate A solution of 84.4 mg of diethyl N-(4-[2-(2-acetamido-4-hydroxypyrido[2,3-d]pyrimidin-6-yl)prop-1-enyl]benzoyl)-L-glutamate in 30 mL of trifluoroacetic acid was hydrogenated at 55 psi of hydrogen in the presence of 0.42 g of 5% Pd/C at room temperature for 24 hours. The catalyst was removed by filtration and the filtrate was evaporated under reduced pressure. The resulting residue was taken up in chloroform and was extracted with a saturated sodium bicarbonate solution. The organic layer was dried over anhydrous sodium sulfate and the solvent was removed under reduced pressure. The residue was then subjected to thin layer chromatography using a 5% methanol:chloroform mixture as the eluent. After elution of a first fraction, there was obtained 19.6 mg of the title compound, NMR (CDCl$_3$ 250 MHz), d 1.20–1.33 (m, overlapping methyls, 9H), 2.45–3.36 (m, 15H), 4.11 (q, 2H, J=7.14 Hz), 4.23 (q, 2H, J=7.10 Hz), 4.89 (m, 1H), 5.44 (brs, 1H), 7.24 (d, 2H, J=7.54 Hz), 7.72 (d, 2H, J=7.54 Hz), 9.77 (brs, 1H), 11.26 (brs, 1H).

EXAMPLE 19

N-(4-[2-(2,4-diaminopyrido[2,3-d]pyrimidin-6-yl)ethyl]benzoyl)-L-glutamic acid

A solution of 0.38 g of diethyl N-(4-[2-(2,4-diaminopyrido[2,3-d]pyrimidin-6-yl)ethyl]benzoyl)-L-glutamate in 50 mL of methanol containing 4.6 mL of 0.5N aqueous sodium hydroxide was stirred at room temperature for 72 hours. Acetic acid (5 mL) was added, and the resulting white precipitate collected by filtration. The filter cake was washed well with water, methanol, and ether and was dried under reduced pressure to yield 0.15 g (44%) of the title compound, which can be alternatively names as 5,10-dideazaaminopterin; mp >250° C.; NMR (TFA-d$_1$) delta 2.2–2.7 (m, 2H), 2.28; 2.7–2.95 (m, 2H), 5.0–5.2 (m, 1H), 7.35 and 7.85 (AB q, 4H, J=9 Hz), 8.7 (s, 1H), 9.1 (s, 1H).

EXAMPLE 20

N-(4-[2-(2,4-diamino-5,6,7,8-tetrahydropyrido[2,3-d]pyrimidin-6-yl)ethyl]benzoyl)-L-glutamic acid Following the procedure of Example 19, hydrolysis of 0.35 g of diethyl N-(4-[2-(2,4-diamino-5,6,7,8-tetrahydropyrido[2,3-d]pyrimidin-6-yl)ethyl]benzoyl)-L-glutamate yielded 0.13 g (42%) of the title compound, which can be alternatively named as 5,10-dideaza-5,6,7,8-tetrahydroaminopterin, mp >250° C.

EXAMPLE 21

N-(4-[2-(2-amino-4-hydroxypyrido[2,3-d]pyrimidin-6-yl)ethyl]benzoyl)-L-glutamic acid A homogeneous solution of 0.175 of diethyl N-(4-[2-(2-acetamido-4-hydroxypyrido[2,3-d]pyrimidin-6-yl)ethyl]benzoyl)-L-glutamate in 50 mL of methanol containing 3 mL of 1N aqueous sodium hydroxide was stirred at room temperature for 72 hours. Addition of 2 mL of acetic acid followed by centrifugation gave 0.125 g (86) of the title compound, which can be alternatively named as 5,10-dideazafolic acid, as a microcrystalline colorless solid, mp >200° C.; NMR (TFA-d$_1$) delta 2.3–2.7 (m, 2H), 2.7–3.0 (m, 2H), 3.25 (s, 5H), 4.9–5.25 (m, 1H), 7.35, 7.85 (AB q, 4H, J=9 Hz), 8.50 (s, 1H), 8.90 (s, 1H).

EXAMPLE 22

N-(4-[2-(2-amino-4-hydroxy-5,6,7,8-tetrahydropyrido[2,3-d]pyrimidin-6-yl)ethyl]benzoyl)-L-glutamic acid Diethyl N-(4-[2-(2-acetamido-4-hydroxy-5,6,7,8-tetrahydropyrido[2,3-d]pyrimidin-6-yl)ethyl]benzoyl)-L-glutamate was hydrolyzed in an analogous fashion to that described in Example 21 to yield the title compound, which can be alternatively named as 5,10-dideaza-5,6,7,8-tetrahydrofolic acid, in 87% yield; mp >250° C., NMR (TFA) delta 1.7–3.9 (m, 13H), 5.0–5.25 (m, 1H), 7.45, 7.85 (AB q, 4H, J=9 Hz).

Similarly obtained from diethyl N-(4-[2-(2-acetamido-4-hydroxypyrido[2,3-d]pyrimidin-6-yl)ethenyl]benzoyl)-L-glutamate was N-(4-[2-(2-amino-4-hydroxypyrido[2,3-d]pyrimidin-6-yl)ethenyl]benzoyl)-L-glutamic acid, mp >200° C.

EXAMPLE 23

N-(4-[1-(2-amino-4-hydroxy-5,6,7,8-tetrahydropyrido[2,3-d]pyrimidin-6-yl)prop-2-yl]benzoyl)-L-glutamic acid A homogeneous solution of 17.5 mg of diethyl N-(4-[1-(2-acetamido-4-hydroxy-5,6,7,8-tetrahydropyrido[2,3-d]pyrimidin-6-yl)prop-2-yl]benzoyl)-L-glutamate in 2 mL of methanolic sodium hydroxide solution was allowed to stand at room temperature for 72 hours. Most of the solvent was then removed under reduced pressure and the mixture was diluted with water and acidified with acetic acid. The precipitate was collected by filtration, washed with water, and dried under reduced pressure (0.1 mm) for 48 hours to give 9.7 mg (67%) of the title compound, which may be alternatively named as 5,10-dideaza-10-methyl-5,6,7,8-tetrahydrofolic acid. mp >250° C., NMR delta 0.87–0.88 (brs, 1H each), 1–2.8 (m, 11H), 3.13 (m, 1H), 4.59 (m, 1H), 6.96 (d, 2H, J=9 Hz), 7.34 (d, 2H, J=9 Hz).

Analogously N-(4-[1-(2-amino-4-hydroxy-5,6,7,8-tetrahydropyrido[2,3-d]pyrimidin-6-yl)but-2-yl]benzoyl)-L-glutamic acid and N-(4-[1-(2,4-diamino-5,6,7,8-tetrahydropyrido[2,3-d]pyrimidin-6-yl)but-2-yl]benzoyl)-L-glutamic acid are prepared.

EXAMPLE 24

In typical models, the indicated tumor cells were implanted subcutaneously in the axillary region of mice. Following intraperitoneal administration of the first compound of Example 22, the length and width of the control tumor (receiving only saline) are measured at the indicated time and compared to those of animals receiving the test compound to calculate percentage of inhibition.

| Tumor System | % INHIBITION Dose mg/kg | | | | Days of Treatment |
|---|---|---|---|---|---|
| | 25 | 50 | 100 | 200 | |
| 6C3HED Lymphosarcoma | 91 | 100 | 100 | 100 | 8 |
| B-16 | 98 | 99 | 100 | 100 | 5 |
| C3H Mammary Adenocarcinoma | 86 | 100 | 100 | 100 | 10 |
| Lewis Lung Carcinoma | 58 | 77 | 94 | 100 | 10 |
| M-5 Ovarian Carcinoma | 12 | 31 | 54 | 80 | 10* |
| Madison Lung | 54 | 72 | 87 | 90 | 10 |
| X5563 Plasma Cell Myeloma | 100 | 100 | 100 | 100 | 10 |

*5 Day Delay Toxic

What is claimed is:

1. A compound selected from the group consisting of:
   (i) 5,6,7,8-tetrahydropyrido[2,3-d]pyrimidines of the formula:

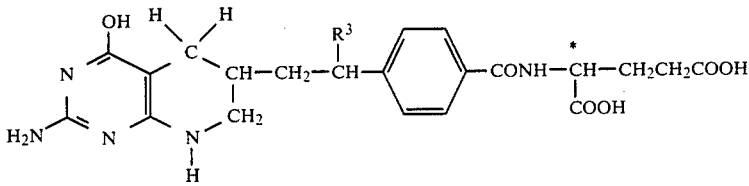

wherein:
R³ is hydrogen, methyl, or ethyl; and
the configuration about the carbon atom designated * is L;
(ii) the tautomeric forms thereof; and
(iii) the pharmaceutically acceptable alkali metal, alkaline earth, non-toxic metal, ammonium, and substituted ammonium salts thereof.

2. The compound according to claim 1 which is N-(4-[2-(2-amino-4-hydroxy-5,6,7,8-tetrahydropyrido[2,3-d]pyrimidin-6-yl)ethyl]benzoyl)-L-glutamic acid.

3. The compound according to claim 1 which is N-(4-[1-(2-amino-4-hydroxy-5,6,7,8-tetrahydropyrido[2,3-d]pyrimidin-6-yl)prop-2-yl]benzoyl)-L-glutamic acid.

4. The compound according to claim 1 which is N-(4-[1-(2-amino-4-hydroxy-5,6,7,8-tetrahydropyrido[2,3-d]pyrimidin-6-yl)but-2-yl]benzoyl)-L-glutamic acid.

5. The method of combating neoplastic growth in a mammal which comprises administering to the mammal in a single or multiple dose regimen an effective amount of a compound according to claim 1.

6. The method of combating neoplastic growth in a mammal which comprises administering to the mammal in a single or multiple dose regimen an effective amount of a compound according to claim 2.

7. A pharmaceutical composition for combating neoplastic growth in a mammal which comprises an amount of a compound according to claim 1 which upon administration to the mammal in a single or multiple dose regimen is effective to combat said growth, in combination with a pharmaceutically acceptable carrier.

8. A pharmaceutical composition for combating neoplastic growth in a mammal which comprises an amount of a compound according to claim 2 which upon administration to the mammal in a single or multiple dose regimen is effective to combat said growth, in combination with a pharmaceutically acceptable carrier.

9. A compound selected from the group consisting of:
(i) 5,6,7,8-tetrahydropyrido[2,3-d]pyrimidines of the formula:

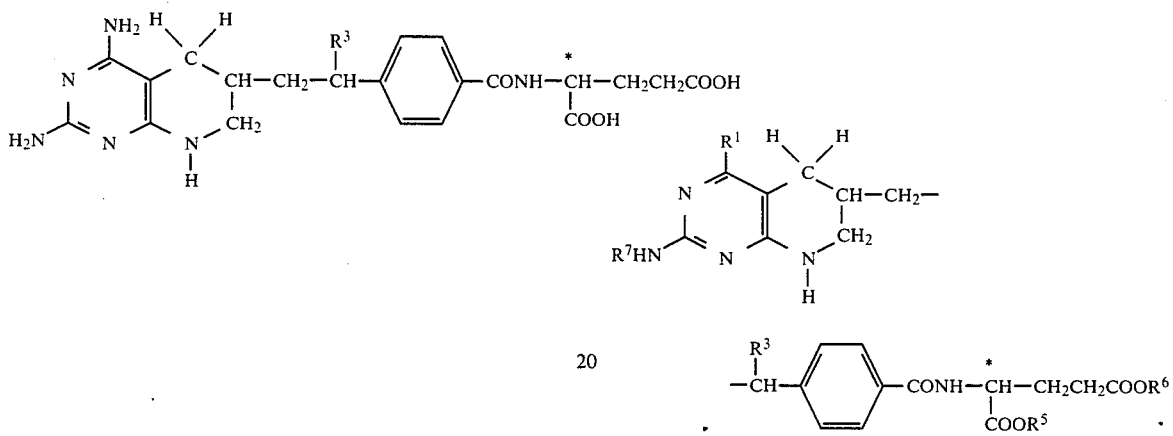

wherein:
R$^1$ is hydrogen, methyl, or ethyl; and
the configuration about the carbon atom designated * is L;
(ii) the tautomeric forms thereof; and
(iii) the pharmaceutically acceptable alkali metal, alkaline earth, non-toxic metal, ammonium, and substituted ammonium salts thereof.

10. The compound according to claim 9 which is N-(4-[2-(2,4-diamino-5,6,7,8-tetrahydropyrido[2,3-d]pyrimidin-6-yl)ethyl]benzoyl)-L-glutamic acid.

11. The compound according to claim 9 which is N-(4-[1-(2,4-diamino-5,6,7,8-tetrahydropyrido[2,3-d]pyrimidin-6-yl)prop-2-yl]benzoyl)-L-glutamic acid.

12. The compound according to claim 9 which is N-(4-[1-(2,4-diamino-5,6,7,8-tetrahydropyrido[2,3-d]pyrimidin-6-yl)but-2-yl]benzoyl)-L-glutamic acid.

13. A compound selected from the group consisting of:
(i) 5,6,7,8-tetrahydropyrido[2,3-d]pyrimidines of the formula:

wherein
R$^1$ is amino or hydroxy;
R$^3$ is hydrogen, methyl, or ethyl;
R$^5$ and R$^6$ are the same or different carboxylic acid protecting group;
R$^7$ is hydrogen or an amino protecting group; and
the configuration about the carbon atom designated * is L; and
(ii) the tautomeric forms thereof.

14. The compound according to claim 13 which is diethyl N-(4-[2-(2-acetamido-4-hydroxy-5,6,7,8-tetrahydropyrido[2,3-d]pyrimidin-6-yl)ethyl]benzoyl)-L-glutamate.

15. The compound according to claim 13 which is diethyl N-(4-[1-(2-acetamido-4-hydroxy-5,6,7,8-tetrahydropyrido[2,3-d]pyrimidin-6-yl)prop-2-yl]benzoyl)-L-glutamate.

16. The compound according to claim 13 which is diethyl N-(4-[2-(2,4-diamino-5,6,7,8-tetrahydropyrido[2,3-d]pyrimidin-6-yl)ethyl]benzoyl)-L-glutamate.

* * * * *